United States Patent
Fiedel et al.

(10) Patent No.: US 9,896,541 B2
(45) Date of Patent: Feb. 20, 2018

(54) HIGHLY ACTIVE DOUBLE METAL CYANIDE CATALYSTS AND METHOD FOR THE PRODUCTION THEREOF

(71) Applicant: Evonik Degussa GmbH, Essen (DE)

(72) Inventors: Olga Fiedel, Essen (DE); Frank Schubert, Neukirchen-Vluyn (DE); Michael Fiedel, Essen (DE); Wilfried Knott, Essen (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 15/312,467

(22) PCT Filed: Apr. 28, 2015

(86) PCT No.: PCT/EP2015/059120
§ 371 (c)(1),
(2) Date: Nov. 18, 2016

(87) PCT Pub. No.: WO2015/176920
PCT Pub. Date: Nov. 26, 2015

(65) Prior Publication Data
US 2017/0088667 A1    Mar. 30, 2017

(30) Foreign Application Priority Data
May 19, 2014  (DE) ......... 10 2014 209 407

(51) Int. Cl.
C07C 43/00  (2006.01)
C08G 65/26  (2006.01)
C07C 41/26  (2006.01)

(52) U.S. Cl.
CPC .......... C08G 65/2663 (2013.01); C07C 41/26 (2013.01)

(58) Field of Classification Search
CPC .................. C08G 65/2663; C07C 41/26

USPC ........................................... 568/622
See application file for complete search history.

(56) References Cited

U.S. PATENT DOCUMENTS

| | | | |
|---|---|---|---|
| 5,290,912 A | 3/1994 | Watabe et al. | |
| 6,051,680 A | 4/2000 | Faraj | |
| 6,348,565 B1 | 2/2002 | Wehmeyer | |
| 6,362,126 B1 | 3/2002 | Grosch et al. | |
| 2010/0105843 A1 | 4/2010 | Knott et al. | |
| 2010/0168367 A1 | 7/2010 | Schubert et al. | |
| 2013/0041115 A1 | 2/2013 | Knott et al. | |
| 2013/0338331 A1* | 12/2013 | Lorenz | C08G 65/2663 528/76 |

FOREIGN PATENT DOCUMENTS

| | | |
|---|---|---|
| EP | 0 485 637 A1 | 5/1992 |
| WO | 99/64152 A1 | 12/1999 |
| WO | 01/90219 A1 | 11/2001 |

OTHER PUBLICATIONS

International Search Report dated Jun. 30, 2015 in PCT/EP2015/059120 filed Apr. 28, 2015.

* cited by examiner

Primary Examiner — Sudhakar Katakam
Assistant Examiner — Kofi Adzamli
(74) Attorney, Agent, or Firm — Philip P. McCann; Smith Moore Leatherwood LLP

(57) ABSTRACT

The invention relates to DMC catalysts comprising polyether siloxanes, to processes for preparation thereof, to the use thereof, and to the DMC catalysts obtainable by the processes according to the invention.

20 Claims, No Drawings

HIGHLY ACTIVE DOUBLE METAL CYANIDE CATALYSTS AND METHOD FOR THE PRODUCTION THEREOF

The invention relates to DMC catalysts comprising polyether siloxanes, to processes for preparation thereof, to the use thereof, and to the DMC catalysts obtainable by the processes according to the invention.

PRIOR ART

The prior art already discloses different processes for preparing double metal cyanide catalysts (DMC catalysts hereinafter) in which surface-active substances are used.

WO 2000/74843 A1 and WO 2000/74845 A1 disclose processes for preparing multimetal cyanide compounds in platelet form and the use thereof for preparation of polyether polyols. For preparation of such multimetal cyanide compounds in platelet form, it is possible to add surface-active components, for example reaction products of fatty alcohols with alkylene oxides, obtainable under the Pluronic® or Plurafac® brand names (products from BASF SE), to the metal salts or the cyano metal compounds. According to the teaching of WO 2000/74843 and of WO 2000/74845, it is thus possible to prepare multimetal cyanide compounds having altered morphology. This platelet-shaped morphology allegedly leads to an increase in the proportion of catalytically active surface area, based on the total surface area, and hence a rise in the mass-specific activity. What is noticeable is that the examples for preparation of polyethers with the DMC catalysts described show exclusively starting of the reaction with propylene oxide.

WO 2004/000913 A1 provides a process for preparing polyether alcohols using DMC catalysts, wherein the DMC catalysts are prepared under very specific reaction conditions, for example with regard to temperature and stirrer output. The DMC catalysts used in this specific process may comprise an organic additive which should be selected from a list of known polymers, preferably from fatty alcohols with alkylene oxides, obtainable under the Pluronic® or Plurafac® brand names (products from BASF SE). In this case too, the examples apparently show only those processes for preparation of polyethers with the DMC catalysts described in which the reaction is started with propylene oxide.

EP1256596 A1 discloses processes for preparing DMC catalysts containing at least one surface-active substance. Equally, WO 00/47650 A1 and EP1165658 A1 are concerned with DMC catalysts containing at least one surface-active substance. In these cases too, exclusively the reaction of propylene oxide is shown with the DMC catalysts obtained.

As is well known, DMC catalysts are used, among other reactions, for alkoxylation of epoxides in particular. This always involves the known epoxides ethylene oxide, propylene oxide and butylene oxide and others. While the starting of the reaction, as is commonly known, can be performed without any problem with propylene oxide and other epoxides of higher molar masses, there are, however, only few experimental examples in which a DMC-catalysed alkoxylation is started with pure ethylene oxide, or pure ethylene oxide-based polyethers are prepared by means of DMC catalysis. The examples in the above-described documents also show the starting of the DMC catalyst with propylene oxide. This is because ethylene oxide acts as a catalyst poison in the majority of the DMC catalysts known from the literature, meaning that it blocks the catalyst, and hence the activity of the catalyst drops severely or stops entirely. It is therefore common practice first to start the catalysts with an epoxide of good compatibility, for example propylene oxide, and to add ethylene oxide only later in the reaction.

There is therefore still a need for catalysts which are less sensitive to comparatively small reactants, for example ethylene oxide, and which preferably simultaneously have good reaction kinetics and short induction periods.

A problem addressed by the present invention was therefore that of providing catalysts which can be started in the presence of ethylene oxide as the sole epoxide. A further problem addressed by the invention was that of providing catalysts which have rapid reaction kinetics and a comparatively short induction period, and which are capable, by virtue of their properties, of distinctly broadening the spectrum of alkoxylation products preparable via DMC catalysis to date.

DETAILED DESCRIPTION

In the context of this invention, it has now been found that DMC catalysts comprising polyether siloxanes solve the stated problems in an excellent manner.

The catalysts of the invention, the process for preparing them, and their use are described below by way of example, without any intention that the invention should be confined to these exemplary embodiments. Where reference is made in what follows to ranges, general formulae or classes of compounds, these shall encompass not just the corresponding ranges or groups of compounds explicitly mentioned, but also all sub-ranges and sub-groups of compounds which are obtainable by extraction of individual values (ranges) or compounds. Where documents are cited in the context of the present description, the content thereof shall fully form part of the disclosure content of the present invention particularly in respect of the substantive matter in the context for which the document was cited. Percentages referred to hereinbelow are by weight unless otherwise stated. Average values referred to hereinbelow are number averages, unless otherwise stated. Physical properties specified below, such as viscosities or the like, for example, are physical properties measured at 25° C. unless otherwise stated. The viscosity is determined at a temperature of 25° C. and a shear rate of 10 1/s with an Anton Paar MCR 301 rheometer.

The present invention therefore provides DMC catalysts preferentially obtainable by the process according to the invention, comprising
  a) one or more double metal cyanide compounds and
  b) one or more polyether siloxanes and
  c) optionally one or more organic complex ligands other than b).

Component a) comprises double metal cyanide compounds which are reaction products of water-soluble metal salts of component a1) and water-soluble metal cyanide salts of component a2).

Water-soluble metal salts of component a1) which are suitable for preparation of the double metal cyanide compounds preferably have the general formula (I)

$$M(X)_n \qquad \text{formula (I)}$$

where M is selected from the metals Zn(II), Fe(II), Ni(II), Mn(II), Co(II), Sn(II), Pb(II), Fe(III), Mo(IV), Mo(VI), Al(III), V(V), V(IV), Sr(II), W(IV), W(VI), Cu(II) and Cr(III). Particular preference is given to Zn(II), Fe(II), Co(II) and Ni(II). X is identical or different, preferably identical, anions, preferably selected from the group of the halides, hydroxides, sulphates, carbonates, cyanates, thiocyanates, isocyanates, isothiocyanates, carboxylates, oxalates and nitrates. The value of n is 1, 2 or 3. Examples of suitable water-soluble metal salts are zinc chloride, zinc bromide, zinc acetate, zinc acetylacetonate, zinc benzoate, zinc nitrate, iron(II) sulphate, iron(II) bromide, iron(II) chloride, cobalt(II) chloride, cobalt(II) thiocyanate, nickel (II) chloride and nickel(II) nitrate. It is also possible to use mixtures of different water-soluble metal salts.

Water-soluble metal cyanide salts of component a2) which are suitable for preparation of the double metal cyanide compounds preferably have the general formula (II)

$$(Y)_a M'(CN)_b (A)_c \qquad (II)$$

where M' is selected from the metals Fe(II), Fe(III), Co(II), Co(III), Cr(II), Cr(III), Mn(II), Mn(III), Ir(III), Ni(II), Rh (III), Ru(II), V(IV) and V(V). More preferably, M' is selected from the metals Co(II), Co(III), Fe(II), Fe(III), Cr(III), Ir(III) and Ni(II). The water-soluble metal cyanide salt may contain one or more of these metals. Y is identical or different, preferably identical, alkali metal cations or alkaline earth metal cations. A is identical or different, preferably identical, anions selected from the group of the halides, hydroxides, sulphates, carbonates, cyanates, thiocyanates, isocyanates, isothiocyanates, carboxylates, oxalates and nitrates. Both a and b and c are integers, where the values of a, b and c are chosen so as to give electronic neutrality of the metal cyanide salt; a is preferably 1, 2, 3 or 4; b is preferably 4, 5 or 6; c preferably has the value of 0.

Examples of suitable water-soluble metal cyanide salts are potassium hexacyanocobaltate(III), potassium hexacyanoferrate(II), potassium hexacyanoferrate(III), calcium hexacyanocobaltate(III) and lithium hexacyanocobaltate (III). Preferred double metal cyanide compounds of component a) are compounds of the general formula (III)

$$M_x[M'_{x'}(CN)_y]_z \qquad (III)$$

in which M is as defined in formula (I) and M' as in formula (II), and x, x', y and z are integers and are chosen so as to give electronic neutrality of the double metal cyanide compound. Preferably, x is 3, x' is 1, y is 6 and z is 2, M is Zn(II), Fe(II), Co(II) or Ni(II) and M' is Co(III), Fe(III), Cr(III) or Ir(III).

Examples of suitable double metal cyanide compounds of component a) are zinc hexacyanocobaltate(III), zinc hexacyanoiridate(III), zinc hexacyanoferrate(III) and cobalt (II) hexacyanocobaltate(III). Further examples of suitable double metal cyanide compounds can be found, for example, in U.S. Pat. No. 5,158,922. Particular preference is given to using zinc hexacyanocobaltate(III).

The polyether siloxane of component b) used may in principle be any polyether siloxane. Polyether siloxanes in the context of this invention are all compounds which contain both a siloxane component and a polyether component. As has been found, DMC catalysts comprising a polyether siloxane of component b) are much more reactive, have fast induction times and are additionally capable of forming pure ethylene oxide polyethers without significant loss of activity. It has been found that particularly fast induction times are possessed especially by those inventive DMC catalysts in which the calculated mean molar mass of the polyether siloxane is from 300 to 50 000 g/mol, preferably from 500 to 30 000 g/mol, more preferably from 600 to 10 000 g/mol, and/or, preferably and, the polyether siloxane has a weight ratio of siloxane component to polyether component of 1:1 to 1:10, preferably 1:1.2 to 1:8, more preferably from 1:1.5 to 1:5, and especially preferably from 1:1.8 to 1:3, based on the calculated mean molar mass of the polyether siloxane. In other words, the quotient which is formed from the calculated mean molar mass of the siloxane component divided by the calculated mean molar mass of the polyether component is from 0.1 to 1, preferably from 0.2 to 0.9, more preferably from 0.4 to 0.6.

The calculated mean molar mass in the context of this invention is determined as follows: Both a $^{29}$Si NMR and a $^1$H NMR of the polyether siloxane used are measured. The $^{29}$Si NMR gives the proportions of M, D, T and Q units. The $^{29}$Si NMR likewise shows whether and how many M and D units on the siloxane are substituted by polyether or other groups. The data thus obtained are used to calculate the molar mass of the siloxane component. Analogously, the $^1$H NMR is used to determine the proportions of the different alkylene oxides in the polyether component and the proportions of the starters. The data thus obtained are used to calculate the molar mass of the polyether component. The two contents give the calculated mean molar mass of the polyether siloxane. $^{29}$Si NMR and $^1$H NMR are measured in CDCl$_3$ as solvent. Alternatively, especially if individual polyether siloxanes should be too complex to calculate their mean molar mass by the above-described method, it is also possible prior to the preparation of the polyether siloxane to determine the polyether by $^1$H NMR prior to the reaction with the siloxane and to calculate its mean molar mass, and to determine the siloxane by $^{29}$Si NMR prior to the reaction with the polyether and to calculate its mean molar mass. The calculated mean molar masses of the two polyether and siloxane starting materials can be used by the person skilled in the art to calculate the mean molar mass of the polyether siloxane product.

To calculate the weight ratio, all polyether radicals up to the binding site to the Si atom (R$^2$ in formula IV) are counted fully as part of the polyether component, and the siloxane skeleton with all the further substituents is counted as part of the siloxane component. Polyether siloxanes having the described weight ratios between polyether component and siloxane component achieve very particularly outstanding DMC catalysts compared to the modified DMC catalysts known in the prior art or to those modified with components b) other than those defined here. Particular preference is given to polyether siloxanes which comprise polydialkylsiloxanes, especially polydimethylsiloxanes, which have 1 to 100 and preferably 1 to 60 D siloxane units and in which the alkyl group, especially the methyl group, at one position has been exchanged for a polyether having 2 to 50 and preferably 3 to 20 alkylene oxide units, preferably ethylene oxide units. In addition, it is preferable when the polyether bears an OH group at the free end (i.e. not the end at which it is bonded to the siloxane).

It may also be particularly advantageous if, as well as the polyether siloxane, a proportion, preferably greater than 0 to 2 molar equivalents, based on the polyether siloxane, of pure polyether is present, corresponding in terms of structure essentially to the polyether of the polyether siloxane.

Preferred polyether siloxanes of component b) correspond to the formula (IV)

$$M_d M'_{d1} D_e D'_{e1} D''_{e2} T_f Q_g \qquad \text{(formula IV)}$$

where
M=(R$^1_3$ Si O$_{1/2}$)
M'=(R$^2$R$^1_2$ Si O$_{1/2}$)
D=(R$^1_2$ Si O$_{2/2}$)
D'=(R$^2$R$^1$ Si O$_{2/2}$)
D''=(R$^4$R$^1$ Si O$_{2/2}$)
T=(R$^3$ Si O$_{3/2}$)
Q=(Si O$_{4/2}$)

d=0 to 20; preferably 1 to 10, more preferably 1 to 5 and especially preferably 2;

d1=0 to 20; preferably 1 to 10, more preferably 0 to 2; especially preferably 0;

where the sum total of d and dl is preferably 2;

e=0 to 300; preferably 1 to 100, more preferably 2 to 40, especially preferably 0 to 20;

e1=0 to 25; preferably 0.1 to 15, more preferably 1 to 10, especially preferably 1 to 5;

e2=0 to 10; preferably 1 to 5, especially preferably 0;

f=0 to 10; preferably 1 to 5, especially preferably 0;

g=0 to 10; preferably 1 to 5, especially preferably 0;

with the proviso that the sum total of dl and el is greater than 0, preferably greater than or equal to 1;

$R^1$ is independently hydrogen or identical or different linear or branched hydrocarbyl radicals having 1 to 30 carbon atoms or else aromatic hydrocarbyl radicals having 6 to 30 carbon atoms, preferably methyl or phenyl, especially methyl;

$R^2$ is independently identical or different polyethers, where the polyethers may have side chains which may optionally also be substituted by further heteroatoms, $R^2$ preferably being selected from the group consisting of

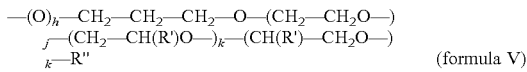     (formula V)

and

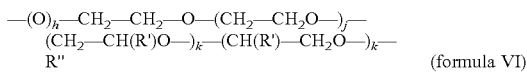     (formula VI)

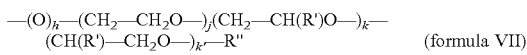     (formula VII)

where h is 0 or 1, preferably 0, j is 0 to 100, preferably greater than 0 to 50, more preferably 2 to 20, especially 3 to 15, k+k'=0 to 100, preferably greater than 0 to 50, especially 2 to 20, especially 0, with the proviso that the sum total of j, k and k' is at least 3 and the units having the indices j, k and k' are arranged in any sequence with respect to one another, i.e. in blockwise or random distribution, in the $R^2$ radical, R' is independently an optionally substituted (substituted, for example, by alkyl radicals, aryl radicals or haloalkyl or haloalkylaryl radicals) alkyl or aryl group having 1 to 12 carbon atoms, preferably ethyl or methyl, especially methyl, and R" is independently a hydrogen radical or an alkyl or alkylene group having 1 to 4 carbon atoms, a —C(O)—R''' group with R'''=alkyl radical, a —CH₂C(O)—CH₂C(O)—R' group, an alkylaryl group, for example a benzyl group, the —C(O)NH—R' group, R" preferably being a hydrogen radical, $R^3$ is independently identical or different $R^1$ or $R^2$ radicals, preferably $R^1$, more preferably methyl or phenyl, especially methyl, $R^4$ is independently identical or different organic radicals having more than 3 carbon atoms, preferably having 4 to 30 and more preferably having 4 to 20 carbon atoms, with the proviso that $R^4$ is different from $R^2$, $R^4$ preferably being selected from —CH₂(CH₂)ₙCH₂—O—CH₂(CHOCH₂), where (CHOCH₂) is an epoxide ring, —CH₂(CH₂)ₙC(O)O—CH₃, —CH₂(CH₂)ₙCH₂OH, —CH₂(CH₂)ₙCH₂—O—CH₂CH(OH)CH₂CH₂(OH) with n=0 to 20, preferably 1 to 10.

The polyethers may be bonded to the siloxane skeleton either via an Si—O—C or via an Si—C bond. Preferably, in the context of this invention, the Si—C compound is as obtained, for example, as the product of the hydrosilylation. In formula (IV), the $R^2$ radical with h=1 is an Si—O—C bond and the preferred h=0 an Si—C bond. Of very particularly outstanding suitability in accordance with the invention are polyether siloxanes of component b) according to formula (IV) with d=2, d1=0, e=0 to 40, e1=1 to 5, e2, f and g=0, $R^1$ methyl, $R^2$=(formula V), (formula VI) and/or (formula VII) with h=0, j=3 to 20, k=0 to 20, preferably 0, R'=methyl or ethyl and R"=hydrogen. According to the invention, it is possible to use all polyether siloxanes obtainable.

DMC catalysts which, according to present invention, contain polyether siloxanes of component b), when used as catalyst, for example in alkoxylations of epoxides, have astonishingly short induction periods and exhibit very good reactivities. Moreover, the catalyst activity thereof is not adversely affected in the case of conversion of high proportions of ethylene oxide or of pure ethylene oxide, especially even right at the start of the reaction. The examples show advances that are astonishing here in the catalyst according to the invention, for example compared to DMC catalysts known from the prior art which have been modified with other surface-active substances, for example with reaction products of fatty alcohols with alkylene oxides.

Organic complex ligands of component c) which may be present in the inventive catalysts are water-soluble organic compounds having heteroatoms, such as oxygen, nitrogen, phosphorus or sulphur, which can form complexes with the double metal cyanide compound. Suitable organic complex ligands are, for example, alcohols, aldehydes, ketones, ethers, esters, amides, ureas, nitriles, sulphides and mixtures thereof. Preferred organic complex ligands are water-soluble aliphatic alcohols such as ethanol, isopropanol, n-butanol, isobutanol, sec-butanol and tert-butanol. Particular preference is given to tert-butanol.

If desired, the inventive catalysts may include, as a further component d), further complex-forming components other than b) and c). Preferably, the complex-forming component d) is a component selected from polyethers, polyesters, polycarbonate, glycidyl ethers, glycoside, carboxylic esters of polyhydric alcohols, polyalkylene glycol sorbitan esters, gallic acid, salts of gallic acid, esters of gallic acid, amide of gallic acid, cyclodextrins, organic phosphate, phosphite, phosphonate, phosphonite, phosphinate or phosphinite, an ionic surface- or interface-active compound and an α,β-unsaturated carboxylic ester. Particular preference is given to polyethers, especially preferably polyethylene glycols or polypropylene glycols, polyethylene glycol and polypropylene glycol ethers, poly(oxyethylene)-co-poly(oxypropylene), poly(oxyethylene)-co-poly(oxypropylene) ethers.

A preferred embodiment of the present invention is therefore DMC catalysts preferentially obtainable by the process according to the invention, comprising a) one or more double metal cyanide compounds and b) one or more polyether siloxanes and c) one or more organic complex ligands other than b), d) one or more complex-forming components other than b) and c), preferably polyethers.

In a further-preferred embodiment of the present invention, DMC catalysts preferentially obtainable by the process according to the invention comprise a) one or more double metal cyanide compounds selected from zinc hexacyanocobaltate(III), zinc hexacyanoiridate(III), zinc hexacyanoferrate(III) and cobalt(II) hexacyanocobaltate(III), b) one or more polyether siloxanes, c) one or more organic complex ligands other than b), selected from aliphatic alcohols, d) optionally one or more complex-forming components other than b) and c), selected from polyethers, polyesters, polycarbonate, glycidyl ethers, glycoside, carboxylic esters of polyhydric alcohols, polyalkylene glycol sorbitan esters, gallic acid, salts of gallic acid, esters of gallic acid, amide of gallic acid, cyclodextrins, organic phosphate, phosphite, phosphonate, phosphonite, phosphinate or phosphinite, an ionic surface- or interface-active compound and an α,β-unsaturated carboxylic ester.

In a very particularly preferred embodiment of the present invention, the DMC catalysts preferentially obtainable by the process according to the invention comprise a) a double metal cyanide compound selected from zinc hexacyanocobaltate(III), zinc hexacyanoferrate(III) and cobalt(II) hexacyanocobaltate(III), and b) one or more polyether siloxanes, preferably of the formula (IV) in which, preferably, the calculated mean molar mass of the polyether siloxane is from 500 to 30 000 g/mol, and the polyether siloxane has a weight ratio of siloxane component to polyether component of 1:1 to 1:10, preferably 1:1.2 to 1:8, more preferably from 1:1.5 to 1:5 and especially preferably from 1:1.8 to 1:3, based on the calculated mean molar mass of the polyether siloxane, more preferably with d=2, d1=0, e=0 to 40, e1=1 to 5, e2, f and g=0, $R^1$=methyl, $R^2$=(formula V), (formula VI) and/or (formula VII) with h=0, j=3 to 20, k=0 to 20, preferably O, R'=methyl or ethyl and R"=hydrogen;

c) one or more aliphatic alcohols, preferably tert-butanol, and d) optionally one or more polyethers, preferably polyethylene glycols or polypropylene glycols.

"Obtainable via the process according to the invention" in the context of this invention means "obtainable by reacting water-soluble metal salts with water-soluble metal cyanide salts to give double metal cyanide compounds of component a), the reaction being effected in the presence of at least one polyether siloxane of component b)". Preferably, the inventive catalysts are "obtainable by reacting water-soluble metal salts of component a1), especially of the formula (I), with water-soluble metal cyanide salts of component a2), especially of the formula (II), in the presence of at least one polyether siloxane of component b), especially of the formula (IV)". Moreover, all products obtainable by the process described hereinafter and preferred embodiments thereof are encompassed.

It is a feature of the process according to the invention for preparing DMC catalysts that, during the preparation of the double metal cyanide compound of component a), which is a reaction product of water-soluble metal salts of component a1) and water-soluble metal cyanide salts of component a2), at least one polyether siloxane of component b) must be present, i.e. must be within the reaction mixture. Thus, the double metal cyanide compound of component a) is formed in the presence of at least one polyether siloxane of component b).

The present invention therefore further provides a process for preparing DMC catalysts in which water-soluble metal salts of component a1), especially of the formula (I), are reacted with water-soluble metal cyanide salts of component a2), especially of the formula (II), in the presence of at least one polyether siloxane of component b), especially of the formula (IV). Preferably, the reaction is effected in the presence of at least one organic complex ligand of component c) other than b). The preferred embodiments of the components a), a1), a2), b), and optionally also c) and/or d) used in this process correspond to the above-described embodiments of the respective components. It has been found that, surprisingly, the presence of at least one polyether siloxane of component b) during the reaction of components a1) and a2) is crucial to the excellent properties of the catalyst. It has been shown in extensive studies that subsequent addition of polyether siloxanes to DMC catalysts described in the prior art, or to DMC catalysts available on the market, cannot achieve the results achieved by the DMC catalysts according to the invention.

The DMC catalysts are typically prepared in aqueous solution by reacting metal salts of component a1), especially of the formula (I), with metal cyanide salts of component a2), especially of the formula (II), in the presence of at least one polyether siloxane of component b) and optionally in the presence of organic complex ligands of component c) and/or one or more further complex-forming components d).

Preferably, in the process according to the invention, the aqueous solutions of the metal salt of component a1), for example zinc chloride, preferably used in a stoichiometric excess (at least 50 mol % based on the metal cyanide salt), and of the metal cyanide salt of component a2), for example potassium hexacyanocobaltate, are first reacted in the presence of at least one polyether siloxane of component b) and optionally in the presence of an organic complex ligand c), for example tert-butanol, forming a dispersion. The polyether siloxane of component b) should preferably be present either in the aqueous solution of the metal salt of component a1) and/or the metal cyanide salt of component a2), but may in principle be added in any other way, provided that it is ensured that the polyether siloxane of component b) is present during the formation of the double metal cyanide compounds of component a), preferably from component a1) and component a2). The organic complex ligand c) may be present in the aqueous solution of the metal salt of component a1) and/or the metal cyanide salt of component a2), or it is added directly to the dispersion obtained after precipitation of the double metal cyanide compound of component a1). Preferably, the dispersion formed is subsequently treated with one or more further complex-forming components d). The further complex-forming component d) can preferably be used in a mixture with water and organic complex ligand c).

For removal of the catalyst particles from the dispersion, it is possible to use any known processes for filtration or sedimentation. The removal can preferably be conducted at temperatures of 10° C. to 80° C. The pressure differentials applied may be 0.001 bar to 200 bar, preferably 0.1 bar to 100 bar, more preferably 0.1 bar to 25 bar, the pressure differential used being dependent on the apparatus used.

Subsequently, the catalyst which has been removed but may still be contaminated by water-soluble by-products can be washed. In the process according to the invention, preference is given to using one or more aqueous solutions of the complex ligand c) and optionally of one or more further complex-forming components d) to conduct a displacement wash. Particular preference is given to washing the moist filtercake first with an aqueous solution of the organic complex ligand c) (for example tert-butanol). In this way, it is possible to remove water-soluble by-products, for example potassium chloride, from the catalyst. In this case, the amount of the organic complex ligand c) in the aqueous washing solution is preferably 40% to 80% by weight, based on the overall solution. It may additionally be preferable to add a little further complex-forming component d) to the aqueous wash solution, more preferably 0.5% to 5% by weight, based on the overall solution. This first wash step may be followed by further wash steps with aqueous or nonaqueous solutions of the organic complex ligand c) and optionally one or more further complex-forming components d).

The DMC catalysts prepared by the process according to the invention, because of their exceptionally high activity, can frequently be used in very low concentrations (25 ppm or less, based on the amount of the polyether polyol to be prepared).

The present invention further provides for the use of the inventive DMC catalysts and of the DMC catalysts prepared in accordance with the invention as catalyst in the preparation of polymers, such as the preparation of polyether polyols, especially in the alkoxylation.

The subject-matter of the present invention is elucidated in detail hereinafter with reference to examples, without any intention that the subject-matter of the invention be restricted to these illustrative embodiments.

EXAMPLES

Chemicals Used:

Zinc chloride (≥98%) and potassium hexacyanocobaltate (III) were purchased from Sigma-Aldrich. tert-Butanol (≥99%) was purchased from Carl Roth. Propylene oxide and ethylene oxide were purchased from GHC Gerling, Holz & CO Handels GmbH. Pluronic® 6100 was purchased from BASF SE.

GPC Measurements:

GPC measurements for determining the polydispersity and weight-average and number-average molar masses Mw and Mn were carried out under the following measurement conditions: Column combination SDV 1000/10 000 Å (length 65 cm), temperature 30° C., THF as mobile phase, flow rate 1 ml/min, sample concentration 10 g/l, RI detector, evaluation of the polyethers was carried out against polypropylene glycol standard (76-6000 g/mol).

Determination of OH Number:

Hydroxyl numbers were determined according to the method DGF C-V 17a (53) of the Deutsche Gesellschaft für Fettwissenschaft [German Society for Fat Science]. This involved acetylating the samples with acetic anhydride in the presence of pyridine and determining the consumption of acetic anhydride by titration with 0.5 N potassium hydroxide solution in ethanol using phenolphthalein.

In the examples which follow, polypropylene glycol (PPG) having a molar mass $M_{OH}$=765 g/mol, which was determined via the OH number, was used as complex-forming component d).

Example A

Preparation of the Double Metal Cyanide Catalysts

Example A1: (Comparative Example)

Without Additive

A multineck flask equipped with a precision glass paddle stirrer, reflux condenser, inert gas inlet and temperature sensor was initially charged with 3.32 g of potassium hexacyanocobaltate(III) dissolved in 40 ml of distilled water, and the mixture was heated to 50° C. under a nitrogen atmosphere. Separately, a solution of 13.63 g of zinc chloride and 20 ml of tert-butanol in 100 ml of distilled water was prepared and added dropwise by means of a dropping funnel to the initially charged solution within about one hour. Subsequently, a further solution consisting of 3.5 g of PPG, 1 ml of distilled water and 20 ml of tert-butanol was added dropwise to the reaction mixture. After a continued stirring period of 10 minutes, the suspension formed was filtered. The filtercake was slurried in the flask in a solution of 40 ml of distilled water and 80 ml of tert-butanol, filtered again, washed with the abovementioned tert-butanol/water mixture and then dried at 70° C. in a drying cabinet overnight. The product obtained was 4.93 g of white powder which was stored over $CaCl_2$ in a desiccator.

Example A2

DMC Preparation Using a Polyether Siloxane Having Siloxane Component 36% by Weight and Polyether Component 64% by Weight A multineck flask with a precision glass paddle stirrer, reflux condenser, inert gas inlet and temperature sensor was initially charged with 3.32 g of potassium hexacyanocobaltate(III) dissolved in 40 ml of distilled water, and the mixture was heated to 50° C. under a nitrogen atmosphere. Separately, a solution of 13.63 g of zinc chloride, 20 ml of tert-butanol and 1 g of a polyether siloxane having siloxane component 36% by weight and polyether component 64% by weight in 100 ml of distilled water was prepared and added dropwise by means of a dropping funnel to the initially charged solution within about one hour. Subsequently, a further solution consisting of 3.5 g of PPG, 1 ml of distilled water, 1 g of a polyether siloxane having siloxane component 36% by weight and polyether component 64% by weight and 20 ml of tert-butanol was added dropwise to the reaction mixture. After a continued stirring period of 10 minutes, the suspension formed was filtered. The filtercake was slurried in the flask in a solution of 40 ml of distilled water and 80 ml of tert-butanol, filtered again, washed with the abovementioned tert-butanol/water mixture and then dried at 70° C. in a drying cabinet overnight. The product obtained was 5.18 g of white powder which was stored over $CaCl_2$ in a desiccator.

Example A3

DMC Preparation Using a Polyether Siloxane Having Siloxane Component 32% by Weight and Polyether Component 68% by Weight A multineck flask equipped with a precision glass paddle stirrer, reflux condenser, inert gas inlet and temperature sensor was initially charged with 3.32 g of potassium hexacyanocobaltate(III) dissolved in 40 ml of distilled water, and the mixture was heated to 50° C. under a nitrogen atmosphere. Separately, a solution of 13.63 g of zinc chloride, 20 ml of tert-butanol and 1 g of a polyether siloxane having siloxane component 32% by weight and polyether component 68% by weight in 100 ml of distilled water was prepared and added dropwise by means of a dropping funnel to the initially charged solution within about one hour. Subsequently, a further solution consisting of 3.5 g of PPG, 1 ml of distilled water, 1 g of a polyether siloxane having siloxane component 32% by weight and polyether component 68% by weight and 20 ml of tert-butanol was added dropwise to the reaction mixture. After a continued stirring period of 10 minutes, the suspension formed was filtered. The filtercake was slurried in the flask in a solution of 40 ml of distilled water and 80 ml of tert-butanol, filtered again, washed with the abovementioned tert-butanol/water mixture and then dried at 70° C. in a drying cabinet overnight. The product obtained was 4.69 g of white powder which was stored over $CaCl_2$ in a desiccator.

Example A4

DMC Preparation Using a Polyether Siloxane Having Siloxane Component 32% by Weight and Polyether Component 68% by Weight Only in PPG Solution (Comparative Example)

A multineck flask equipped with a precision glass paddle stirrer, reflux condenser, inert gas inlet and temperature sensor was initially charged with 3.32 g of potassium hexacyanocobaltate(III) dissolved in 40 ml of distilled water, and the mixture was heated to 50° C. under a nitrogen atmosphere. Separately, a solution of 13.63 g of zinc chloride and 20 ml of tert-butanol in 100 ml of distilled water was prepared and added dropwise by means of a dropping funnel to the initially charged solution within about one hour. Subsequently, a further solution consisting of 3.5 g of PPG, 1 ml of distilled water, 1 g of a polyether siloxane having siloxane component 32% by weight and polyether component 68% by weight and 20 ml of tert-butanol was added dropwise to the reaction mixture. After a continued stirring period of 10 minutes, the suspension formed was filtered. The filtercake was slurried in the flask in a solution of 40 ml of distilled water and 80 ml of tert-butanol, filtered again, washed with the abovementioned tert-butanol/water mixture and then dried at 70° C. in a drying cabinet overnight. The product obtained was 4.5 g of white powder which was stored over $CaCl_2$ in a desiccator.

Example A5

DMC Preparation Using a Polyether Siloxane Having Siloxane Component 32% by Weight and Polyether Component 68% by Weight Only in Wash Solution (Comparative Example)

A multineck flask equipped with a precision glass paddle stirrer, reflux condenser, inert gas inlet and temperature sensor was initially charged with 3.32 g of potassium hexacyanocobaltate(III) dissolved in 40 ml of distilled water, and the mixture was heated to 50° C. under a nitrogen atmosphere. Separately, a solution of 13.63 g of zinc chloride and 20 ml of tert-butanol in 100 ml of distilled water was prepared and added dropwise by means of a dropping funnel to the initially charged solution within about one hour. Subsequently, a further solution consisting of 3.5 g of PPG, 1 ml of distilled water and 20 ml of tert-butanol was added dropwise to the reaction mixture. After a continued stirring period of 10 minutes, the suspension formed was filtered. The filtercake was slurried in the flask in a solution of 40 ml of distilled water, 1 g of a polyether siloxane having siloxane component 32% by weight and polyether component 68% by weight and 80 ml of tert-butanol, filtered again and then dried at 70° C. in a drying cabinet overnight. The product obtained was 5.07 g of white powder which was stored over $CaCl_2$ in a desiccator.

Example A6

DMC Preparation Using Pluronic® 6100 (Comparative Example)

A multineck flask equipped with a precision glass paddle stirrer, reflux condenser, inert gas inlet and temperature sensor was initially charged with 3.32 g of potassium hexacyanocobaltate(III) dissolved in 40 ml of distilled water, and the mixture was heated to 50° C. under a nitrogen atmosphere. Separately, a solution of 13.63 g of zinc chloride, 20 ml of tert-butanol and 1 g of Pluronic® 6100 in 100 ml of distilled water was prepared and added dropwise by means of a dropping funnel to the initially charged solution within about one hour. Subsequently, a further solution consisting of 3.5 g of PPG, 1 ml of distilled water, 1 g of Pluronic® 6100 and 20 ml of tert-butanol was added dropwise to the reaction mixture. After a continued stirring period of 10 minutes, the suspension formed was filtered. The filtercake was slurried in the flask in a solution of 40 ml of distilled water and 80 ml of tert-butanol, filtered again, washed with the abovementioned tert-butanol/water mixture and then dried at 70° C. in a drying cabinet overnight. The product obtained was 5.01 g of white powder which was stored over CaCl2 in a desiccator.

Example B

Preparation of Polyether Polyols

In the examples which follow, the starter polyether used, by way of example, was poly(oxypropylene) monobutyl ether having molar mass $M_{OH}$=384 g/mol, which was determined via the OH number. In principle, the syntheses can be conducted with any starter which has one or more hydroxyl groups and is suitable for use in DMC-catalysed reactions.

Induction time is understood to mean the period in which the starting amount of propylene oxide (60 g) initially charged for activation of the catalyst is fully consumed. The consumption of the monomer is monitored by means of a manometer. The consumption is complete when the pressure in the reactor after the addition of PO declines to the starting pressure (the pressure value before the starting amount of PO has been added). The total reaction time includes the induction period and the reaction time that was taken thereafter to convert the residual monomer.

Example B1

Comparative Example—Catalyst From Example A1

A 5 liter autoclave was initially charged with 255 g of poly(oxypropylene) monobutyl ether (M=384 g/mol) as starter and 96 mg of DMC catalyst A1, and heated to 130° C. while stirring. The reactor was evacuated to an internal pressure of 30 mbar in order to distillatively remove any volatile ingredients present. To activate the DMC catalyst, a portion of 60 g of propylene oxide was introduced. After the reaction had started and the internal pressure had dropped, firstly a further 325 g of propylene oxide were metered in with cooling. This was followed by 40 minutes of continued reaction at 130° C. with subsequent degassing. This removed volatile components such as residual propylene oxide by distillation under reduced pressure at 130° C. The virtually colourless alkoxylation product was cooled to below 90° C. and discharged from the reactor.

According to GPC, the product had a weight-average molar mass of 1042 g/mol and a polydispersity Mw/Mn of 1.09. The OH number determined is 61.0.
Induction period: 72 min
Total reaction time: 139 min Example B2

Catalyst From Example A2

The experiment was conducted analogously to Example 1. The catalyst used was DMC catalyst A2.

According to GPC, the product had a weight-average molar mass of 976 g/mol and a polydispersity Mw/Mn of 1.04. The OH number determined is 55.0.
Induction period: 15 min
Total reaction time: 89 min Example B3

Catalyst From Example A3

The experiment was conducted analogously to Example 1. The catalyst used was DMC catalyst A3.

According to GPC, the product had a weight-average molar mass of 993 g/mol and a polydispersity Mw/Mn of 1.05. The OH number determined is 58.9.
Induction period: 15 min
Total reaction time: 53 min Example B4

Catalyst From Example A4 (Comparative Example)

The experiment was conducted analogously to Example 1. The catalyst used was DMC catalyst A4.

According to GPC, the product had a weight-average molar mass of 1002 g/mol and a polydispersity Mw/Mn of 1.11. The OH number determined is 56.2.
Induction period: 33 min
Total reaction time: 74 min Example B5

Catalyst From Example A5 (Comparative Example)

The experiment was conducted analogously to Example 1. The catalyst used was DMC catalyst A5.

According to GPC, the product had a weight-average molar mass of 1018 g/mol and a polydispersity Mw/Mn of 1.06. The OH number determined is 54.6.
Induction period: 20 min
Total reaction time: 74 min The results of the alkoxylation experiments show that reactions in which inventive DMC catalysts A3 and A2 were used have shorter induction times compared to the catalyst without addition of polyether siloxanes. Moreover, catalysts where the polyether siloxane was added not during the precipitation of the zinc hexacyanocobaltate complex but in a later step in the course of synthesis thereof exhibit a longer induction time and are thus less catalytically active.

In addition, tests were conducted where the DMC catalyst was activated by feeding in a portion of 40 g of ethylene oxide.

Example B6

Catalyst From Example A1

A 5 liter autoclave was initially charged with 255 g of poly(oxypropylene) monobutyl ether as starter and 96 mg of DMC catalyst A1, and heated to 130° C. while stirring. The reactor was evacuated to an internal pressure of 30 mbar in order to distillatively remove any volatile ingredients present. To activate the DMC catalyst, a portion of 40 g of ethylene oxide was introduced. After the reaction had started up and the internal pressure had dropped, at first a further 252 g of ethylene oxide were metered in. Since no pressure decrease in the reactor was observed, the addition of ethylene oxide was stopped and the reactor was deodorized.

Example B7

Catalyst From Example A2

A 5 liter autoclave was initially charged with 255 g of poly(oxypropylene) monobutyl ether as starter and 96 mg of DMC catalyst A2, and heated to 130° C. while stirring. The reactor was evacuated to an internal pressure of 30 mbar in order to distillatively remove any volatile ingredients present. To activate the DMC catalyst, a portion of 40 g of ethylene oxide was introduced. After the reaction had started up and the internal pressure had dropped, at first a further 252 g of ethylene oxide were metered in while cooling. This was followed by 40 minutes of continued reaction at 130° C. with subsequent degassing. This removed volatile components such as residual ethylene oxide by distillation under reduced pressure at 130° C. The alkoxylation product was cooled to below 90° C. and discharged from the reactor.

According to GPC, the product had a weight-average molar mass of 783 g/mol and a polydispersity Mw/Mn of 1.1. The OH number determined is 72.5.
Induction period: 27 min Example B8

Catalyst From Example A3

A 5 liter autoclave was initially charged with 255 g of poly(oxypropylene) monobutyl ether as starter and 96 mg of DMC catalyst A3, and heated to 130° C. while stirring. The reactor was evacuated to an internal pressure of 30 mbar in order to distillatively remove any volatile ingredients present. To activate the DMC catalyst, a portion of 40 g of ethylene oxide was introduced. After the reaction had started up and the internal pressure had dropped, at first a further 252 g of ethylene oxide were metered in while cooling. This was followed by 40 minutes of continued reaction at 130° C. with subsequent degassing. This removed volatile components such as residual ethylene oxide by distillation under reduced pressure at 130° C. The alkoxylation product was cooled to below 90° C. and discharged from the reactor.

According to GPC, the product had a weight-average molar mass of 810 g/mol and a polydispersity Mw/Mn of 1.09. The OH number determined is 72.8.
Induction period: 24 min Example B9

Catalyst From Example A6

A 5 liter autoclave was initially charged with 255 g of poly(oxypropylene) monobutyl ether as starter and 96 mg of DMC catalyst A6, and heated to 130° C. while stirring. The reactor was evacuated to an internal pressure of 30 mbar in order to distillatively remove any volatile ingredients present. To activate the DMC catalyst, a portion of 40 g of ethylene oxide was introduced. After the reaction had started up and the internal pressure had dropped, a further 252 g of ethylene oxide were metered in while cooling, and a decrease in the reaction rate was recorded in the course of the polymerization. This was followed by 40 minutes of continued reaction at 130° C. with subsequent degassing. This removed volatile components such as residual ethylene oxide by distillation under reduced pressure at 130° C. The alkoxylation product was cooled to below 90° C. and discharged from the reactor. According to GPC, the product had a weight-average molar mass of 929 g/mol and a polydispersity Mw/Mn of 1.11. The OH number determined is 69.0.

Induction period: 44 min

Example B10

Catalyst from Example A4

A 5 liter autoclave was initially charged with 255 g of poly(oxypropylene) monobutyl ether as starter and 96 mg of DMC catalyst A4, and heated to 130° C. while stirring. The reactor was evacuated to an internal pressure of 30 mbar in order to distillatively remove any volatile ingredients present. To activate the DMC catalyst, a portion of 40 g of ethylene oxide was introduced. After the reaction had started up and the internal pressure had dropped, at first further ethylene oxide was metered in while cooling. After the 252 g of ethylene oxide had already been added, the internal pressure in the reactor did not fall completely to the original value, and so a residual amount of EO had to be distilled off at the end of the polymerization.

Example B11

Catalyst From Example A5

A 5 liter autoclave was initially charged with 255 g of poly(oxypropylene) monobutyl ether as starter and 96 mg of DMC catalyst A5, and heated to 130° C. while stirring. The reactor was evacuated to an internal pressure of 30 mbar in order to distillatively remove any volatile ingredients present. To activate the DMC catalyst, a portion of 40 g of ethylene oxide was introduced. Since, after 130 min, the internal pressure did not drop to the original value and did not decrease any further either, the residual amount of EO was distilled off and the polymerization reaction was stopped.

The results of the ethoxylation experiments show that reactions in which DMC catalysts A3 and A2 were used have shorter induction times compared to catalyst A6 which was synthesized using a different surfactant. What is also noticeable is that catalyst A1 which was prepared without addition of polyether siloxanes did not exhibit any catalytic activity in the ethoxylation. Equally inactive were catalysts where the polyether siloxane was added not during the precipitation of the zinc hexacyanocobaltate complex but in a later step in the course of synthesis thereof.

The invention claimed is:

1. A double metal cyanide catalyst, comprising: a double metal cyanide compound, and a polyether siloxane wherein the double metal cyanide compound is a compound of general formula (III) $M_x[(M'_x(CN)_y]_z$ (III) wherein M is at least one metal selected from the group consisting of Zn(II), Fe(II), Co(II) and Ni(II) and M' is at least one metal selected from the group consisting of Co(III), Fe(III), Cr(III) and Ir(III), with wherein x is 3, x' is 1, y is 6 and z is 2.

2. The double metal cyanide according to claim 1, wherein the polyether siloxane has a weight ratio of a siloxane component to a polyether component of 1:1 to 1:10, based on a calculated mean molar mass of the polyether siloxane.

3. The double metal cyanide catalyst according to claim 1, wherein the polyether siloxane is a polyether siloxane of general formula (IV)

$$M_dM'_{d1}D_eD'_{e1}D''_{e2}T_fQ_g \qquad \text{(formula IV)}$$

wherein M is $(R^1_3SiO_{1/2})$; M' is $(R^2R^1_2SiO_{1/2})$;
D is $(R^1_2SiO_{2/2})$;
D' is $(R^2R^1SiO_{2/2})$;
D'' is $(R^4R^1SiO_{2/2})$;
T is $(R^3SiO_{3/2})$;
Q is $(SiO_{4/2})$;
d is 0-20; d1 is 0-20;
e is 0-300; e1 is 0 to 25; e2 is 0 to 10;
f is 0 to 10;
g is 0 to 10;
wherein the sum of d1 and e1 is greater than 0, and wherein each $R^1$ is independently a hydrogen or a linear or branched hydrocarbyl radical having 1 to 30 carbon atoms or an aromatic hydrocarbyl radical radicals having 6 to 30 carbon atoms; each $R^2$ is independently a polyether, wherein the polyether optionally comprises side chains which are optionally substituted with heteroatoms, each $R^3$ is independently a $R^1$ or $R^2$ radical, each $R^4$ is independently an organic radical having 4 to 30 carbon atoms, with the proviso that $R^4$ is different from $R^2$.

4. The double metal cyanide catalyst according to claim 3, wherein each $R^2$ in general formula (IV) is independently a polyether of at least one formula selected from the group consisting of formula V, formula VI, and formula VII

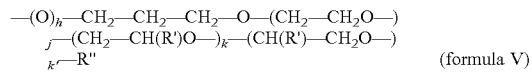

$$\text{—(O)}_h\text{—CH}_2\text{—CH}_2\text{—CH}_2\text{—O—(CH}_2\text{—CH}_2\text{O—)}_j\text{—(CH}_2\text{—CH(R')O—)}_k\text{—(CH(R')—CH}_2\text{O—)}_{k'}\text{—R''} \qquad \text{(formula V)}$$

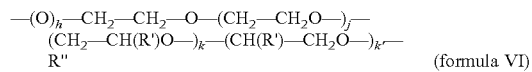

$$\text{—(O)}_h\text{—CH}_2\text{—CH}_2\text{—O—(CH}_2\text{—CH}_2\text{O—)}_j\text{—(CH}_2\text{—CH(R')O—)}_k\text{—(CH(R')—CH}_2\text{O—)}_{k'}\text{—R''} \qquad \text{(formula VI)}$$

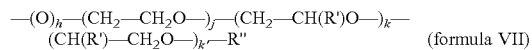

$$\text{—(O)}_h\text{—(CH}_2\text{—CH}_2\text{O—)}_j\text{—(CH}_2\text{—CH(R')O—)}_k\text{—(CH(R')—CH}_2\text{O—)}_{k'}\text{—R''} \qquad \text{(formula VII)}$$

wherein h is 0 or 1, j is 0 to 100, k+k' is 0 to 100, with the proviso that the sum of j, k and k' is at least 3, wherein each R' is independently an optionally substituted alkyl or aryl group having 1 to 12 carbon atoms, and each R'' is independently a hydrogen radical or an alkyl group having 1 to 4 carbon atoms.

5. The double metal cyanide catalyst according to claim 4, wherein the polyether siloxane is a polyether siloxane of general formula (IV) wherein d is 2, d1 is 0, e is 0 to 40, e1 is 1 to 5, e2 is 0, f is 0, g is 0, each $R^1$ is methyl, each $R^2$ is a polyether of at least one formula selected from the group consisting of (formula V), (formula VI) and (formula VII) wherein h is 0, j is 3 to 20, k is 0 to 20, each R' is methyl or ethyl and each R'' is hydrogen.

6. A double metal cyanide catalyst comprising a double metal cyanide compound, and a polyether siloxane of general formula (IV)

$$M_dM'_{d1}D_eD'_{e1}D''_{e2}T_fQ_g \qquad \text{(formula IV)}$$

wherein M is $(R^1_3SiO_{1/2})$; M' is $(R^2R^1_2SiO_{1/2})$;

D is $(R^1{}_2SiO_{2/2})$;
D' is $(R^2R^1SiO_{2/2})$;
D" is $(R^4R^1SiO_{2/2})$;
T is $(R^3SiO_{3/2})$;
Q is $(SiO_{4/2})$;
d is 0-20; d1 is 0-20;
e is 0-300; e1 is 0 to 25; e2 is 0 to 10;
f is 0 to 10;
g is 0 to 10;
  wherein the sum of d1 and e1 is greater than 0, and wherein each $R^1$ is independently a hydrogen or a linear or branched hydrocarbyl radical having 1 to 30 carbon atoms or an aromatic hydrocarbyl radical radicals having 6 to 30 carbon atoms; each $R^2$ is independently a polyether, wherein the polyether optionally comprises side chains which are optionally substituted with heteroatoms, each $R^3$ is independently a $R^1$ or $R^2$ radical, each $R^4$ is independently an organic radical having 4 to 30 carbon atoms, with the proviso that $R^4$ is different from $R^2$.

7. The double metal cyanide catalyst according to claim 1, one or more organic complex ligands which are different than the polyether siloxane and which is organic complex ligand selected from the group consisting of alcohols, aldehydes, ketones, ethers, esters, amides, ureas, nitriles, and sulphides.

8. The double metal cyanide catalyst according to claim 7, wherein the double metal cyanide compound is selected from the group consisting of zinc hexacyanocobaltate(III), zinc hexacyanoiridate(III), zinc hexacyanoferrate(III) and cobalt(II) hexacyanocobaltate(III), the one or more organic complex ligands which are different than the polyether siloxane are aliphatic alcohols, and the double metal cyanide catalyst optionally further comprises one or more complex-forming components which are different from the polyether siloxane and the organic complex ligands which are at least one selected from the group consisting of polyethers, polyesters, a polycarbonate, glycidyl ethers, glycoside, carboxylic esters of polyhydric alcohols, polyalkylene glycol sorbitan esters, gallic acid, salts of gallic acid, esters of gallic acid, an amide of gallic acid, cyclodextrins, organic phosphate, phosphite, phosphonate, phosphonate, phosphinate, or phosphinite, an ionic surface- or interface-active compound and an α,β-unsaturated carboxylic ester.

9. The double metal cyanide catalyst according to claim 1 which is obtained by reacting a water-soluble metal salt with a water-soluble metal cyanide salt thereby forming the double metal cyanide compound, wherein the reacting is performed in the presence of the polyether siloxane.

10. A process for preparing a double metal cyanide catalyst, the process comprising: reacting a water-soluble metal salt with a water-soluble metal cyanide salt thereby forming a double metal cyanide compound, wherein the reacting is performed in the presence of a polyether siloxane thereby forming the double metal cyanide catalyst wherein the double metal cyanide compound is a compound of general formula (III)

$$M_x[M'_{x'}(CN)_y]_z \qquad\qquad (III)$$

wherein M is at least one metal selected from the group consisting of Zn(II), Fe(II), Co(II) and Ni(II) and M' is at least one metal selected from the group consisting of Co(III), Fe(III), Cr(III) and Ir(III), with wherein x is 3, x' is 1, y is 6 and z is 2.

11. The process according to claim 10, wherein the polyether siloxane has a weight ratio of a siloxane component to a polyether component of 1:1 to 1:10, based on a calculated mean molar mass of the polyether siloxane.

12. The process according to claim 10, wherein the water soluble metal salt is a water-soluble metal salt of general formula (I)

$$M(X)_n \qquad\qquad \text{formula(I)}$$

wherein M is at least one metal selected from the group consisting of Zn(II), Fe(II), Co(II) and Ni(II), each X is independently at least one anion selected from the group consisting of halides, hydroxides, sulphates, carbonates, cyanates, thiocyanates, isocyanates, isothiocyanates, carboxylates, oxalates and nitrates, and n is 2; wherein the water-soluble metal cyanide salt is a water-soluble metal cyanide salt of general formula (II)

$$(Y)_aM'(CN)_b(A)_c \qquad\qquad \text{formula(II)}$$

wherein M' is at least one metal selected from the group consisting of Co(II), Co(III), Fe(II), Ir(III) and Ni(II), each Y is independently an alkali metal cation or an alkaline earth metal cation, each A is independently at least one anion selected from the group consisting of halides, hydroxides, sulphates, carbonates, cyanates, thiocyanates, isocyanates, isothiocyanates, carboxylates, oxalates and nitrates, and a is 1, 2, 3 or 4; b is 4, 5 or 6, c is 0, 1 or 2, with the proviso that the metal cyanide salt is electronically neutral; and wherein the polyether siloxane is a polyether siloxane of general formula (IV)

$$M_dM'_{d1}D_eD'_{e1}D''_{e2}T_fQ_g \qquad\qquad \text{(formula IV)}$$

wherein M is $(R^1{}_3SiO_{1/2})$; M' is $(R^2R^1{}_2SiO_{1/2})$; D is $(R^1{}_2SiO_{2/2})$; D' is $(R^2R^1SiO_{2/2})$; D" is $(R^4R^1SiO_{2/2})$; T is $(R^3SiO_{3/2})$; Q is $(SiO_{4/2})$ d is 0 to 20; d1 is 0 to 20; e is 0 to 300; e1 is 0 to 25; e2 is 0 to 10; f is 0 to 10; g is 0 to 10; wherein the sum of d1 and e1 is greater than 0; and wherein each $R^1$ is independently a linear or branched hydrocarbyl radical having 1 to 30 carbon atoms or an aromatic hydrocarbyl radical having 6 to 30 carbon atoms; each $R^2$ is independently a polyether, wherein the polyether optionally comprises side chains which are optionally substituted with heteroatoms, each $R^3$ is independently a $R^1$ or $R^2$ radical, each $R^4$ is independently an organic radical radicals having 4 to 30 carbon atoms, with the proviso that $R^4$ is different from $R^2$.

13. The process according to claim 12, wherein each $R^2$ in general formula (IV) is independently a polyether of at least one formula selected from the group consisting of formula V, formula VI, and formula VII

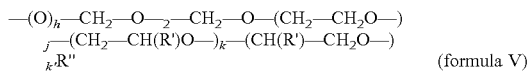
(formula V)

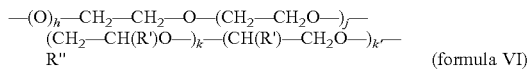
(formula VI)

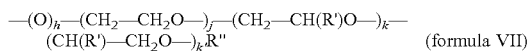
(formula VII)

wherein h is 0 or 1, j is 0 to 100, k+k' is 0 to 100, with the proviso that the sum of j and k is at least 3, and wherein each R' is independently an substituted alkyl or aryl group having 1 to 12 carbon atoms, and each R" is independently a hydrogen radical or an alkyl group having 1 to 4 carbon atoms.

14. The process according to claim 12, wherein the water-soluble metal salt is selected from the group consisting of zinc chloride, zinc bromide, zinc acetate, zinc acetylacetonate, zinc benzoate, zinc nitrate, iron(II) sulfate, iron (II) bromide, iron(II) chloride, cobalt(II) chloride, cobalt(II) thiocyanate, nickel(II) chloride, and nickel(II) nitrate, and the water-soluble metal cyanide salt is at least one selected from the group consisting of potassium hexacyanocobaltate (III), potassium hexacyanoferrate(II), potassium hexacyanoferratee(III), calcium hexacyanocobaltate(III), and lithium hexacyanocobaltate(III).

15. A method, comprising: preparing a polymer in the presence of the double metal cyanide catalyst according to claim 1.

16. The process according to claim 12, wherein the reacting is performed in the presence of at least one organic complex ligand that is different than the polyether siloxane and which is at least one organic complex ligand selected from the group consisting of alcohols, aldehydes, ketones, ethers, esters, amides, ureas, nitriles, and sulphides.

17. The process according to claim 13, wherein the water-soluble metal salt is selected from the group consisting of zinc chloride, zinc bromide, zinc acetate, zinc acetylacetonate, zinc benzoate, zinc nitrate, iron(II) sulfate, iron (II) bromide, iron(II) chloride, cobalt(II) chloride, cobalt(II) thiocyanate, nickel(II) chloride, and nickel(II) nitrate; the water-soluble metal cyanide salt is at least one selected from the group consisting of potassium hexacyanocobaltate(III), potassium hexacyanoferrate(II), potassium hexacyanoferrate(III), calcium hexacyanocobaltate(III), and lithium hexacyanocobaltate(III); and the polyether siloxane is a polyether siloxane of general formula (IV) wherein d is 2 d1 is 0, e is 0 to 40, e1 is 1 to 5, e2 is 0, f is 0, g is 0, each R1 is methyl, each R2 is a polyether of at least one formula selected from the group consisting of (formula V), (formula VI) and (formula VII) wherein h is 0, j is 3 to 20, k is 0 to 20, each R' is methyl or ethyl, and each R" is hydrogen.

18. A method, comprising: preparing a polymer in the presence of a double metal cyanide catalyst obtained by a process according to claim 10.

19. A double metal cyanide catalyst, comprising: a double metal cyanide compound having a compound of general formula (III)

$$M_x[(M'_{x'}(CN)_y]_z \quad (III)$$

wherein M is at least one metal selected from the group consisting of Zn(II), Fe(II), Co(II) and Ni(II) and M' is at least one metal selected from the group consisting of Co(III), Fe(III), Cr(III) and Ir(III), with wherein x is 3, x' is 1, y is 6 and z is 2; a polyether siloxane which has a weight ratio of a siloxane component to a polyether component of 1:1 to 1:10 based on a calculated mean molar mass of the polyether siloxane; and an organic complex ligand which is different than the polyether siloxane and which is at least one organic complex ligand selected from the group consisting of alcohols, aldehydes, ketones, ethers, esters, amides, ureas, nitriles, and sulphides; wherein the catalyst has a lower induction time in an alkoxylation of an epoxide relative to an otherwise identical catalyst lacking the polyether siloxane.

20. The double metal cyanide catalyst of claim 19, wherein the epoxide comprises ethylene oxide, the induction time is less than 30 minutes, or both.

* * * * *

UNITED STATES PATENT AND TRADEMARK OFFICE
CERTIFICATE OF CORRECTION

PATENT NO. : 9,896,541 B2  
APPLICATION NO. : 15/312467  
DATED : February 20, 2018  
INVENTOR(S) : Olga Fiedel et al.

Page 1 of 1

It is certified that error appears in the above-identified patent and that said Letters Patent is hereby corrected as shown below:

In the Claims

Column 16,
Line 67, "Formula (III) $M_x[(M'_x(CN)_y]_z$" should read -- Formula (III) $M_x[(M'_{x'}(CN)_y]_z$ --.

Column 18,
Line 19, "Co(III), Fe(II), Ir(III)" should read -- Co(III), Fe(II), Fe(III), Ir(III) --.

Column 20,
Line 11, "$M_x[(M'_{x'})(CN)_y]$" should read -- $M_x[(M'_{x'})(CN)_y]_z$ --.

Signed and Sealed this  
Tenth Day of April, 2018

Andrei Iancu  
*Director of the United States Patent and Trademark Office*